(12) United States Patent
Gestrelius et al.

(10) Patent No.: US 7,897,180 B2
(45) Date of Patent: *Mar. 1, 2011

(54) ENAMEL MATRIX PROTEIN COMPOSITION FOR TREATMENT OF SYSTEMIC INFLAMMATORY RESPONSE

(75) Inventors: Stina Gestrelius, Lund (SE); Petter Lyngstadaas, Nesoddtangen (NO)

(73) Assignee: Institut Straumann AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/575,086

(22) Filed: Oct. 7, 2009

(65) Prior Publication Data

US 2010/0093632 A1 Apr. 15, 2010

Related U.S. Application Data

(63) Continuation of application No. 10/242,684, filed on Sep. 12, 2002, now Pat. No. 7,608,284.

(60) Provisional application No. 60/323,286, filed on Sep. 19, 2001.

(30) Foreign Application Priority Data

Sep. 14, 2001  (DK) .............................. 2001 01340

(51) Int. Cl.
*A61K 35/32* (2006.01)
(52) U.S. Cl. ..................... 424/549; 424/548; 514/2; 514/21
(58) Field of Classification Search ................ None
See application file for complete search history.

(56) References Cited

U.S. PATENT DOCUMENTS 6,503,539 B2   1/2003   Gestrelius et al.
6,720,009 B2   4/2004   Gestrelius et al.
6,979,670 B1   12/2005  Lyngstadaas et al.

FOREIGN PATENT DOCUMENTS

CN     1297356 A      5/2001
RU     2050158 C1    12/1995
WO     WO 99/43344    9/1999

OTHER PUBLICATIONS

P. Nikolopoulos et al., "J. Clin. Periodontol", 25:715-720 (1998).
S. Foster, "Journal Of Bacteriology", 174(s): 464-470 (1992).
S. Gestrelius et al., "J. Clin Periodontol", 24:685-692 (1997).
A. Hoang, et al., "Periodontol", 71(8):1270-1277 (2000).

*Primary Examiner*—Allison M Ford
(74) *Attorney, Agent, or Firm*—Rissman Hendricks & Oliverio LLP (57) ABSTRACT

The present invention relates to the use of a preparation of an active enamel matrix substance, such as an amelogenin, for the manufacture of a pharmaceutical composition for modulating an immune response. The composition can be used in preventing and/or treating a condition or disease in a mammal that is characterised by said mammal presenting an imbalance in its native immune response to an internal and/or external stimuli, i.e. wherein at least a part of said mammal's immune system is stimulated non-discriminatingly, reacts hypersensitively to said immunogen, or fails to react to said stimuli. Said condition can typically either be systemic or local, such as a systemic and/or post-traumatic whole-body inflammation or an autoimmune disease.

19 Claims, 3 Drawing Sheets

ENAMEL MATRIX PROTEIN COMPOSITION FOR TREATMENT OF SYSTEMIC INFLAMMATORY RESPONSE

FIELD OF THE INVENTION

The present invention relates to the use of a preparation of an active enamel matrix substance, such as an amelogenin, a processed amelogenin product, or a metabolite thereof, for the manufacture of a pharmaceutical composition for modulating an immune response. The composition can be used in preventing and/or treating a condition or disease in a mammal that is characterised by said mammal presenting an imbalance in its native immune response to an internal and/or external stimuli. Said condition can typically either be systemic or local, such as a systemic and/or post-traumatic whole-body inflammation or an autoimmune disease.

BACKGROUND OF THE INVENTION

The normal function of the immune system is to protect the body by attacking and destroying foreign microorganisms, such as bacteria and viruses. Under normal conditions, these would be recognised as invaders and thus be rendered harmless.

Responsible for a subject's immune response is the lymphoid system; meaning the assemblage of lymphocytes, their precursors and derivatives, and all supportive cells. Under abnormal conditions or imbalance of the immune system, it fails to react and destroy the foreign microorganisms, mistakes own cells and tissues as foreign and attacks them, or is activated inappropriately in a hypersensitive manner.

An immune response to an antigenic agent, be it a foreign antigen or an auto-antigen, is generally characterised by the production of antibodies by B lymphocytes, and destruction of any cells displaying those antigens by T lymphocytes or natural killer (NK) cells. Defects in B or T lymphoid cells, however, may result in the development of immunodeficiency diseases or the impairment of the immune response function. The immune deficiency or defect may be congenital, i.e. caused by a mutation in a gene, or it may be acquired, e.g. through a viral infection or as a result of the ageing process. The thus produced defect may or may not be fatal, depending on the stage of stem cell or lymphocyte differentiation at which it occurs.

In addition to an antigen, lymphocytes need lymphokines for full activation. E.g., the T-helper cells do not proliferate unless they receive signals from macrophages, and T-cytotoxic cells as well as B-cells depend on signals from T-helper cells and probably also from macrophages for their full development. An adequate immune response needs the co-ordinated activities of several cell types, which means that modulating the expression or activity of lymphokines potentially has a beneficial effect on adverse immune responses.

After shocks, burns, extensive surgical procedures or traumatic injury, functions of the immune system can be overstimulated within a systemic, non-discriminant, excessive whole-body inflammation, whereas other functions are dramatically paralysed. When the immunological host response is thus uncontrolled, the unbalanced states of cellular activation that are observed lead to consecutive clinical states. Such states can be acute-phase response, whole-body inflammation, anergy, sepsis, infection or organ failure and may finally lead to multiple organ failure. Multiple organ failure or dysfunction is the most common cause for death in intensive care units. As of today, therapy directed to prevent or improve uncontrolled immune response has not been able to dramatically alter the outcome.

Other examples for unbalanced situations are when the immune system attacks its own body. These situations differ in the origin of the antigen that triggers the attack and the mechanisms and manifestations of the attack. These reactions are often referred to as allergy, delayed-type hypersensitivity, allograft, and autoimmune reactions, respectively.

Anergy is another unbalanced condition, in which the body fails to react to an injected allergen or antigen. Anergy is thought to be the result of intercellular signalling after interaction between T-cell receptor (TCR) and peptide-presenting major histocompatibility complex (MHC) antigen in the absence of a "costimulatory" signal. This costimulatory signal is normally provided on the cell surface of antigen-presenting cells (APCs).

The immune system modulates its function both locally and systemically. E.g. delayed-type hypersensitivity can manifest itself either locally in a characteristic skin reaction, or in a systemic reaction in which large quantities of the antigen enter the bloodstream and which is characterised by fever, malaise, pains in the joints and reduction of the number of circulating lymphocytes. Inflammation is generally defined as a local response to cellular injury, whereas whole body inflammation or multiple organ failure is a systemic inflammation.

Posttraumatically, monocytes and macrophages are immediately hyperactivated to excessively release proinflammatory cytokines. This excessive release results in the development of whole body inflammation, followed in most patients by substantial paralysis of cell function. After 3 to 5 days this state is overcome with newly recruited monocytes/macrophages that probably lack the full spectrum of activity, though, because they are immature. In addition, patients can also undergo an anti-inflammatory phase (the compensatory anti-inflammatory response syndrome), and at times a mixed response with both pro- and anti-inflammatory components (the mixed antagonistic response syndrome) is observed.

The posttraumatic impact on the balance of cell-mediated immune regulation is thus primarily caused by a simultaneous attack on the monocyte/macrophage lineage and T cells, causing disintegration of the intact cell interaction. Traumatic stress not only effects the capacity of adequate and specific performance of each cell type; it also effects control capacity and modulatory surveillance that the monocyte/macrophage lineage and T cells normally posses for each other within a number of regulatory loops. This loss of regulatory function occurs instantaneously at the moment of injury.

Known inflammatory cytokines to cause the above-described initial systemic hyperinflammation are e.g. Tumour necrosis factor-a (TNF-alpha), Interleukin-1 (IL-1), IL-6, and Interferon gamma, which might act synergistically with TNF-alpha. Clinical trials aimed at down-regulating these mediators, using e.g. antibodies against endotoxin, TNF-alpha, antagonists of IL-1, or platelet activating factor, have so far been uniformly disappointing. Not only have these agents been found to have no regulating effect, they even increased mortality.

Furthermore, under stressful conditions, the monocyte/macrophage lineage's are easily triggered to produce and release prostaglandin $E_2$ ($PGE_2$), which is probably the most powerful endogenous immune suppressant. $PGE_2$ is an inhibitor of T cell mitogenesis, IL-2 receptor expression and IgM antibody synthesis by B cells. Via intracellular elevation of cAMP levels, $PGE_2$ also negatively controls the monocyte/ macrophage lineage synthesis of TNFα and IL-1. $PGE_2$ can inhibit the synthesis of $TH_1$ cytokines (IL-2, IFNγ) but not the synthesis of IL-4 by $TH_2$ cells. Thus $PGE_2$ secretion may tip the balance in favour of a $TH_2$ type response, leading to a switch in B cell production from IgM to IgG1 and IgE. Tipping the balance thus influences the development of a $TH_1$ or a $TH_2$-dominated response.

Traditional reagents and methods used to regulate a patient's immune response often result in unwanted side effects. For example, immunosuppressive reagents, such as cyclosporine A, azathioprine and prednisone are used to suppress the immune system of a patient with an autoimmune disease or patients receiving transplants. Such reagents, however, suppress a patient's entire immune response, thereby crippling the ability of the patient to mount an immune response against infectious agents not involved in the original disease. Due to such harmful side effects and the medical importance of immune regulation, reagents and methods to regulate specific parts of the immune system have been the subjects of study for many years.

Enamel matrix proteins, present in the enamel matrix, are most well known as precursors to enamel. Prior to cementum formation, enamel matrix proteins are deposited on the root surface at the apical end of the developing tooth-root. The deposited enamel matrix is the initiating factor for the formation of cementum. Again, the formation of cementum in itself is associated with the development of the periodontal ligament and the alveolar bone. As shown by the present inventors prior to the present invention, enamel matrix proteins can therefore promote periodontal regeneration through mimicking the natural attachment development in the tooth (Gestrelius S, Lyngstadaas S P, Hammarström L. Emdogain-periodontal regeneration based on biomimicry. Clin Oral Invest 4:120-125 (2000).

The enamel matrix is composed of a number of proteins, such as amelogenin, enamelin, tuft protein, proteases, and albumin. Amelogenins, the major constituent of the enamel matrix, are a family of hydrophobic proteins derived from a single gene by alternative splicing and controlled post secretory processing. They are highly conserved throughout vertebrate evolution and demonstrate a high overall level of sequence homology among all higher vertebrates examined (>80%). In fact, the sequences of porcine and human amelogenin gene transcript differ only in 4% of the bases. Thus, enamel matrix proteins, although of porcine origin, are considered self when encountered in the human body and can promote dental regeneration in humans without triggering allergic responses or other undesirable reactions.

Enamel matrix proteins and enamel matrix derivatives (EMD) have previously been described in the patent literature to be able to induce hard tissue formation (i.e. enamel formation, U.S. Pat. No. 4,672,032 (Slavkin)), binding between hard tissues (EP-B-0 337 967 and EP-B-0 263 086) and wound healing, such as of skin and mucosa (WO 99/43344).

SUMMARY OF THE INVENTION

The present invention is based on the surprising finding that active enamel substances have the ability to modulate immune mechanisms of mammals. Immunomodulation herein being defined as an increase or decrease in the level of immune response brought about by various specific and non-specific means.

A preferred embodiment of the present invention thus comprises the use of an active enamel substance for the manufacture of a pharmaceutical composition for the prevention and/or treatment of a condition in a mammal, wherein said condition is characterised by an imbalance in the immune response of said mammal to an immunogen, such as an external or internal stimulatory factor.

An "imbalance in the immune response" can occur after shocks, burns, extensive surgical procedures and/or traumatic injury. The term describes a situation/condition, wherein one or more functions of the immune system can be either over-stimulated within a systemic, nondiscriminant, excessive whole-body inflammation, whereas other functions can simultaneously or independently be under-stimulated. The term "imbalance in the immune response" describes a situation/condition in which the immunological host response is uncontrolled, and wherein the unbalanced states of cellular activation that are observed lead to consecutive clinical states. Such states can be acute-phase response, whole-body inflammation, anergy, shock, sepsis, infection and/or organ failure and may finally lead to multiple organ failure.

Other examples for "imbalance in the immune response" are situations/conditions wherein the subject's inert immune system attacks its own body. These situations differ in the origin of the antigen that triggers the attack and the mechanisms and manifestations of the attack. These reactions are often referred to as allergy, delayed-type hypersensitivity, allograft, and autoimmune reactions, respectively.

The term "imbalance in the immune response" can describe both local and systemic situations, as described above. E.g. Inflammation is generally defined as a local response to cellular injury, whereas whole body inflammation or multiple organ failure are examples of systemic inflammation.

In the present context, the term "an immunogen" is used to describe any factor that is able to elicit an immune response. This can e.g. be a toxin, fungus, parasite, virus, bacteria, pollen, dust, pollution particle, cytokine, hormone, stress, surgery, burn, transplanted organ or blood, tissue graft, shock, trauma, or a non-self or a self antigen.

Immunological hypersensitivity reactions are immune responses which lead to tissue damage or impaired body function. They are classified into five types (I-V), according to the mechanism of the tissue damage, they are involved in many important human diseases and disorders, such as anaphylaxis, asthma, food allergies, myasthenia gravis and systemic lupus erythematosus.

In one embodiment of the present invention, an active enamel substance is used for the manufacture of a pharmaceutical composition for the prevention and/or treatment of a condition in a mammal, wherein at least a part of the immune system reacts hypersensitively to said immunogen. In a preferred embodiment, at least a part of the immune system of said mammal is thus stimulated non-discriminatingly.

The conditions which may benefit from the invention comprise conditions wherein the imbalance of the immune response of said mammal is either local and/or systemic. In the present context systemic is defined as relating to or common to a system, i.e. affecting the body generally, in contrast to being local. Said condition can e.g. be an auto-immune disease selected from the group consisting of rheumatoid arthritis, diseases of the skin, allergy, sclerosis, arteriosclerosis, multiple sclerosis, asthma, psoriasis, lupus, systemic lupus erythematosis, diabetes mellitus, myasthenia gravis, chronic fatigue syndrome, fibromyalgia, chronic fatigue syndrome, Crohn's disease, Hashimoto's thyroiditis, Grave's disease, Addison's disease, Guillian Barre syndrome and scleroderma.

In the present context, the term "autoimmune disease" refers to a wide variety of over 80 different serious chronic illnesses. Autoimmune diseases are the third major category of illness in the United States, behind cancer and heart disease. Between 75-90% of all autoimmune diseases occur in women and usually within the childbearing years. In addition to body organs, autoimmune diseases also affect nerves, muscles, blood, connective tissues, gastrointestinal system and all body systems.

The cause of autoimmune diseases is not fully known or understood, however, it is suspected that hormones, heredity and environmental factors play a major role in their cause and onset. The courses of most of these diseases are individualised and highly unpredictable. Autoimmune diseases do not represent generalised failures in the tolerance mechanism, rather they reflect the appearance of a specific response to a specific self-antigen.

Other conditions equally envisioned in the present invention are characterised as systemic inflammations and/or infections and can be associated with trauma, burns, surgery, dialysis, shock and/or bacterial or viral infection, in a preferred embodiment of the invention, the systemic condition is associated with a disease selected from the group consisting of extracorporeal membrane oxygenation (ECMO), shock, systemic inflammatory response syndrome (SIRS), sepsis, multi organ failure, rejection of an implant such as organ and/or prostheses, heart and lung bypass surgery, chronic inflammation, asthma and/or stress related disease in the lung, bacterial infection, gangrene, soft tissue infection, and wound infection.

Several severe trauma, such as major surgery, systemic inflammation, burns, or shock can result in massive impairment of immunological reactivity in a patient, the clinical consequence of which is high susceptibility of the traumatised individual towards serious systemic infection that can lead to massive tissue destruction and organ failure.

In one embodiment of the present invention, active enamel substances are thus used for the manufacture of a pharmaceutical composition for the prevention and/or treatment of a condition in a mammal, wherein at least part of the immune system attacks molecules, cells, or tissues of the organism producing them. Active enamel substances are herein used for the manufacture of a pharmaceutical composition for the prevention and/or treatment of a condition in a mammal, wherein the condition is characterised as a systemic inflammation and/or infection.

Within a systemic, nondiscriminant, excessive whole-body inflammation, parts of the immune system are stimulated, whereas other functions within the complex of cell-mediated immunity (CMI) are dramatically paralysed. Immune abnormalities in the aftermath of trauma occur in a sequence of states of cellular activation and within a complex order of events, that is not yet well understood. One known fact is that traumatic stress causes disintegration of the intact monocyte-T cell interaction, which is associated with profound changes in monocyte regulation and substantial depression of T cell function. In a preferred embodiment of the present invention, active enamel substances are thus used for the manufacture of a pharmaceutical composition for restoring the balance in the monocyte-T cell interaction of a patient, i.e. for restoring a healthy monocyte regulation and T cell function.

In the current context, inflammation is defined as a local response to cellular injury that is marked by capillary dilatation, leukocytic infiltration, redness, heat, pain, swelling, and/or loss of function and that normally serves as a mechanism initiating the elimination of noxious agents and of damaged tissue.

Active enamel substances are in the present invention used for the manufacture of a pharmaceutical composition for the modulation of the conception of T-helper cell activation in a mammal. The active enamel substance comprised in the pharmaceutical composition can herein modulate the level of expression, release and/or function of either inter- and/or intra-cellular signalling substances. The active enamel substance comprised in the pharmaceutical composition can alternatively modulate the level of expression, release and/or function of at least one cytokine involved in the immune mechanism of said mammal or modulate a cellular signalling cascade involved in the immune mechanism of said same mammal.

Many common and clinically important disease states, such as rheumatoid arthritis, asthma, tuberculosis, leprosy, schistosomiasis, chronic hepatitis, thyroiditis and multiple sclerosis, are examples of chronic inflammation and its consequences. Chronic inflammation may result from failure to eliminate an acute inflammatory irritant, from an autoimmune response to a self-antigen, or may be caused by an innately chronic irritant of low intensity that persists. It is characterised by simultaneous inflammation and repair, with recruitment and activation of macrophages, lymphocytes and other cells triggered by the co-ordinated action of cytokines and growth factors. A preferred embodiment of the present invention comprises the use of an active enamel substance for the manufacture of a pharmaceutical composition for the treatment and/or prevention of chronic inflammation.

Chronic inflammation is most appropriately defined in terms of the process, in which continuing inflammation and attempted tissue healing by repair occur simultaneously. Although it is often defined simply in terms of time course, with lesions of over 6 weeks' duration traditionally being regarded as chronic, any such definition is entirely arbitrary. At a microscopic level, chronic inflammation is sometimes defined in terms of the pattern of cellular response, although this is variable and not altogether reliable.

The distinctive features of this process are best appreciated by comparing it with the acute inflammatory response. In contrast to acute inflammation, where the host response leads to elimination of the irritant, followed by recovery involving tissue regeneration or repair, chronic inflammation is characterised by inflammation and repair occurring concurrently, rather than consecutively. Repair is always a feature of chronic inflammation because it is associated with irritants that cause destruction of tissue architecture. Repair is typically achieved by ingrowth of granulation tissue, which includes macrophages, fibroblasts and new blood vessels.

Other important distinctions between acute and chronic inflammation relate to the relative balance between exudation and cellular recruitment, as well as the types of cells that predominate in the inflammatory response. In chronic inflammation there is typically a less pronounced exudative response and increased inflammatory cellular recruitment, which may be accompanied by local cellular proliferation. In contrast to acute inflammation, which is usually characterised by recruitment of large numbers of neutrophil leukocytes, the dominant infiltrating cell in all forms of chronic inflammation is the macrophage. Depending on the nature of the irritant, different profiles of inflammatory mediators and growth factors (collectively referred to as cytokines) are generated locally, giving rise to different morphological patterns of chronic inflammation.

The systemic effects of inflammation are more pronounced in chronic inflammatory diseases and may contribute significantly to the clinical consequences. These systemic effects are largely mediated by cytokines. Whereas the most prominent systemic effects of acute inflammation are fever and leukocytosis, chronic inflammation is usually associated with fatigue, sleepiness, weight loss and wasting.

When the condition and/or disease related to in the present invention is characterised as an infection, said condition can be caused by a contamination with a bacterium selected from but not limited to the group consisting of gram negative microbes and gram positive microbes 1) G+: E.g. *Staphylococci* and *streptococci*, which are able to release the endotoxin peptidoglycan (PepG) that is a specific cell wall component of G+ microbes. 2) G−: E.g. *coli*-forms and other microbes releasing lipopolysaccharides (LPS) from their outer cell envelope during infection. The immunological condition is herein caused by an endo-toxin and/or an exo-toxin, produced by said infecting microbe.

In the present invention, cellular responses in human blood, caused by endo-toxins from *Staphylococcus aureus* (PepG) and *Escherichia coli* (LPS) are effectively modulated by administration of amelogenins, as shown in example 1. These results clearly demonstrate the potential modulatory effect of active enamel substances on the immune mechanism in mammals.

In another experiment, conducted by the inventors and documented in the present application as example 2, using a pig model for sepsis, the therapeutic potential of enamel matrix derivatives is examined in vivo.

EMD, even delivered by big bolus injections, is in experiment 2 shown to be safe to administer systemically in high dosages. Moreover, it is herein proven that systemic injections of enamel matrix derivatives counteract the effect of endotoxin (LPS) in pigs. Generally, it can be concluded that the onset of septic shock in the treated pigs are delayed, compared to sham operated pigs. The delay is dependent on dosage, 1 mg/kg bodyweight only gives a short delay (about 30 minutes) while a dosage 5 mg/kg seems to protect against, or at least significantly delay (>5 hours), the onset of septic shock and the related multi-organ failures.

One possible mechanism that could explain the beneficial effect of enamel matrix derivatives on LPS induced shock is that enamel matrix derivatives bind LPS and thus inactivates the toxic effect. Another, equally envisable possibility is that enamel matrix derivatives compete with LPS for the same receptor(s) on e.g. white blood cells, macrophages, osteoclasts and/or mastcells. Thus, a preferred embodiment of the invention relates to the use of an active enamel substance for the preparation of a pharmaceutical composition, wherein said active enamel substance inactivates the toxic effect of an endo-toxin and/or exo-toxin produced by a microbe, by binding directly to said endo-toxin and/or exo-toxin, and/or by binding to the cellular receptor for said endo-toxin and/or exo-toxin.

A third and highly probable possible mechanism is that enamel matrix derivatives modulate the immune response directly by regulating, in a favourable way, the expression cascade of cytokines and signal molecules that are major players in the LPS induced septic shock. Based on previous ex vivo experiments not described in the present application, it seems reasonable to ascribe at least part of the enamel matrix derivatives' effect to the latter mechanism. Furthermore, the blood analyses performed also suggest that enamel matrix derivatives have a direct effect on cytokine expression in white blood cells. The effect appears to be specific, having a strong effect on TNF and IL-6, but non on IL-1β. Finally, it is well possible that all the mechanisms proposed above are involved, and that it is the combination of these effects that give the beneficial effect of enamel matrix derivatives in this model.

The delay of the onset of septic shock, reported in example 2, has significant clinical value. In one envisioned embodiment of the invention, the delay is directly related to the amount of "free" LPS in the blood, and enamel matrix derivatives will thus be delivered as an adjunct to antibiotics in severe bacteraemia and infections like meningitis, to delay and/or reduce the effect of toxins. Such treatment will be crucial for the survival of the patient in the critical hours, following the start of antibiotic treatment.

In another, equally preferred embodiment, the effect of enamel matrix derivatives is caused by direct modulation of the inflammatory response, and thus enamel matrix derivatives might be used in a wide array of clinical situations in which shock is a possible complication. This includes all major surgery, transplantations, trauma, ECMO, acute dialysis, severe infections, severe allergies and many more.

Without the intention to limit the scope of the present invention, one theoretical explanation for the mechanism by which an active enamel substance as described herein is able to modulate the immune system of a mammal, is its interaction with a cell surface receptor and/or a cell surface structure, selected from the group consisting of ICAM, HLA antigen, Interleukin 1 receptor, Interleukin 2 receptor, Interleukin 3 receptor, Interleukin 4 receptor, Interleukin 5 receptor, Interleukin 6 receptor, Interleukin 7 receptor, Interleukin 8 receptor, Interleukin 9 receptor, Interleukin 10 receptor, Interleukin 11 receptor, Interleukin 12 receptor, Interleukin 13 receptor, Interleukin 14 receptor, Interleukin 15 receptor, Interleukin 16 receptor, Interleukin 17 receptor, Interleukin 18 receptor, IFNα receptor, IFNβ receptor, IFNΔ receptor, IFNγ receptor, IFNΩ receptor PDGF receptors, TGF receptors, TNF receptor, EGF receptor, the CD44 variants and the integrine receptor family.

Cell surface receptors are well known mediators of cellular communication, when activated by their respective signalling molecule, the ligand. The cell surface receptor binds the ligand with high or low affinity and converts this extracellular event into one or more intracellular signals that alter the behaviour of the target cell. Active enamel substances may thus be able to modulate the immune system by altering the behaviour of the target cell through a similar manner. Thus, in one embodiment of the present invention, active enamel substances activate a cell surface receptor, thereby inducing a receptor specific intercellular signalling cascade and altering the expression of one or more genes leading to an alteration of the behaviour of said cell.

In another embodiment of the present invention, an active enamel substance can activate a cell surface receptor that operates directly as an enzyme, a so called catalytic receptor, an example being a transmembrane protein with a cytoplasmic domain that functions as a tyrosine kinase.

In yet another preferred embodiment of the present invention, an active enamel substance activates a G-protein-linked surface receptor that indirectly activates or inactivates a separate plasma membrane bound enzyme or an ion channel. The interaction between the receptor and the enzyme and/or ion channel is typically mediated by a third protein such as a G protein (GTP-binding regulatory protein), which activates intracellular mediators, such as but not limited to cyclic AMP, InsP3 and $Ca^{2+}$.

Cytokines like Interleukins, IFNγ and TNFα all play a critical role in the regulation of the immune response. Particular interest has been centred on cytokine gene regulation as part of T cell differentiation into the $TH_1$ and $TH_2$ subsets. The effect of a cytokine can e.g. be mediated through its specific receptor that initiates a signal transduction pathway, which can in itself result in the release of cytokines in a feedback mechanism.

As demonstrated in example 1, amelogenin has modulatory effects on the cytokine release and regulation of inflammatory surface receptors in response to bacterial cell wall products. An embodiment of the present invention thus encloses the use of an active enamel substance for the manufacture of a pharmaceutical composition for modulating an immune response by mediating a signal through a cytokine receptor, such as IL-2R, IL-4R, IL-10R, IFNγR and TNFαR. Alternatively, as the release of cytokines is regulated by the level of their expression, an active enamel substance can also modulate an immune response by initiating an up- and/or down-regulation of the expression level of one or more cytokine(s) in a mammal, thereby modulating the release and/or function of one or more cytokine(s).

In an especially preferred embodiment of the present invention, an active enamel substance mediates a regulation of an immune response through a TNFαR. TNFα receptors are expressed on all somatic cell types with the exception of erythrocytes. Two receptors of 55 kDa (TNF-R1; also designated: CD120a, also referred to as TNF receptor superfamily member 1A (TNF-RSF1A) and 75 kDa (TNF-R2; also designated: CD120b, also referred to as TNF receptor superfamily member 1B (TNF-RSF1B) have been described. TNFαR is related to the low affinity receptor of NGF and to human cell surface antigen CD40 and is expressed strongly on stimulated T-cells and B-lymphocytes. A third receptor subtype is expressed in normal human liver. It binds TNFα but not TNFβ.

Differential effects of the two receptor subtypes have been found. It appears that engagement of the p55 receptor specifically leads to the induction of the cellular adhesion molecules ICAM-1, E-selectin, V-CAM-1, and CD44, while engagement of both the p55 and the p75 receptor induces expression of α-2 integrine. Apart from the membrane-bound receptors, several soluble proteins that bind TNF have been described. These proteins of approximately 30 kDa, called T-BP-1 and T-BP-2 (tumour necrosis factor binding proteins), are derived from the TNF-binding domain of the membrane receptor. They probably function as physiological regulators of TNF activities by inhibiting binding of TNF to its receptor.

The biological activities of IL-2 are mediated by a membrane receptor that is expressed almost exclusively on activated, but not on resting, T-cells. IL-5 and IL-6 modulate the expression of the IL-2 receptor. In another preferred embodiment of the present invention, an active enamel substance is envisioned that mediates a regulation of an immune response through an IL-2R.

Three different types of IL-2 receptors are distinguished that are expressed differentially and independently. The high affinity IL-2 receptor constitutes approximately 10 percent of all IL-2 receptors expressed by cells. This receptor is a membrane receptor complex consisting of the two subunits IL-2R-alpha (TAC antigen=T-cell activation antigen; p55) and IL-2R-beta (p75; new designation: CD122). p75 is expressed constitutively on resting T-lymphocytes, NK-cells, and a number of other cell types while the expression of p55 is usually observed only after cell activation. p75 is involved in IL-2-mediated signal transduction. In addition, the IL-2 receptor is associated with a number of other proteins (p22, p40, p100) which are thought to be involved in mediating conformational changes in the receptor chains, receptor-mediated endocytosis, and further signal transduction processes. One of the identified proteins is the 95 kDa cell adhesion molecule ICAM-1 which probably focuses IL-2 receptors at regions of cell-to-cell contacts and thus may mediate paracrine activities, for example, during IL-2-mediated stimulation of T-cells. Another protein associated with p75 is a tyrosine-specific protein kinase called lck, other kinases may be associated also with IL-2 receptors. Two such kinases, called fyn and lyn, have been identified. In addition, IL-2 receptor signalling may be mediated also by vav. A third 64 kDa subunit of the IL-2 receptor, designated gamma, has been described recently. This subunit is required for the generation of high and intermediate affinity IL-2 receptors but does not bind IL-2 by itself. The gamma subunit of the IL-2 receptor has been shown recently to be a component of the receptors for IL-4 and IL-7. It is probably also a component of the IL-13 receptor.

Activated lymphocytes continuously secrete a 42 kDa fragment of the TAC antigen. This fragment circulates in the serum and plasma and functions as a soluble IL-2 receptor (sIL-2R). The concentrations of this soluble receptor varies markedly in different pathological situations.

In another preferred embodiment of the present invention, an active enamel substance activates the IFNγR. A number of binding proteins with molecular masses between 70 and 160 kDa have been described for IFNγR. They are expressed on all types of human cells with the exception of mature erythrocytes. The receptor expressed in monocytes and other haematopoietic cells has a molecular mass of 140 kDa. A 54 kDa protein is observed in other cell types.

The biological activities of IL-4 are mediated by the IL-4 receptor (IL-4R). In a preferred embodiment of the present invention, an active enamel substance activates the IL-4R. The extracellular domain of the IL-4 receptor is related to the receptors for Epo, IL-6 and the beta chain of the IL-2 receptor. It has been given the nameCD124. Two forms of the receptor have been described, one of which is secreted. The secreted receptor only contains the extracellular IL-4 binding domain and is capable of blocking IL-4 activities. An IL-4 binding protein (IL-4-BP) that binds IL-4 with the same affinity as the IL-4 receptor has been shown to be a soluble IL-4 receptor variant. Soluble receptors probably function as physiological regulators of cytokine activities by inhibiting receptor binding or by acting as transport proteins. The mechanisms of IL-4-mediated intracellular signal transduction are largely unknown. IL-4 influences intracellular calcium levels and also the metabolism of inositol phospholipids and protein kinase C.

In humans, IL10 is produced by activated CD8$^+$ peripheral blood T-cells, by Th$_0$, Th$_1$-, and Th$_2$-like CD4$^+$ T cell clones after both antigen-specific and polyclonal activation, by B-cell lymphomas, and by LPS-activated monocytes and mast cells. IL-4 and IL10 inhibit the synthesis of IL10 by monocytes. In a preferred embodiment of the present invention, an active enamel substance activates the IL-10 receptor (IL-10R). The murine IL-10 receptor has been cloned. This receptor is a protein of approximately 110 kDa that binds murine IL-10 specifically. This receptor is structurally related to receptors for IFN.

The effect of enamel matrix derivatives on peripheral lymphocytes showed that the porcine amelogenin derivative Emdogain® induces a slight increase of the proliferation of CD25/CD4 positive lymphocytes in vitro, and a concomitant decrease of CD19 positive B-lymphocytes (Petinaki, E., S. Nikolopoulos, and E. Castanas. 1998. Low stimulation of peripheral lymphocytes, following in vitro application of Emdogain. 3 Clin Periodontol. 25:715-20). The authors could not demonstrate any significant influence on immunoglobulin and/or cytokine (IL-2 and IL-6) production, though.

Interestingly, the inventors have observed that various cell cultures of fibroblasts (embryonic, dermal, derived from the periodontal ligament, fish fin or bird skin), produce twice as much transforming growth factor (TGF-β1) when stimulated with EMDOGAIN® (BIORA AB, SWEDEN), compared to non-stimulated cultures. These findings support the concept of the potential modulatory influence of active enamel substances on imbalanced immune responses.

Enamel matrix is a precursor to enamel and may be obtained from any relevant natural source, i.e. a mammal in which teeth are under development. A suitable source is developing teeth from slaughtered animals such as, e.g., calves, pigs or lambs. Another source is e.g. fish skin.

Enamel matrix can be prepared from developing teeth as described previously (EP-B-0 337 967 and EP-B-0 263 086). The enamel matrix is scraped off and enamel matrix derivatives (EMD) are prepared, e.g. by extraction with aqueous solution such as a buffer, a dilute acid or base or a water/solvent mixture, followed by size exclusion, desalting or other purification steps, alternatively followed by freeze-drying. Enzymes may alternatively be deactivated by treatment with heat or solvents, in which case the derivatives may be stored in liquid form without freeze-drying.

As an alternative source of the enamel matrix derivatives or proteins one may also use generally applicable synthetic routes, well known to a person skilled in the art, or use cultivated eukaryotic and/or prokaryotic cells, alternatively modified by DNA-techniques. The enamel matrix proteins may thus be of recombinant origin and alternatively genetically modified (see, e.g., Sambrook, J. et al.: Molecular Cloning, Cold Spring Harbor Laboratory Press, 1989).

In the present context, enamel matrix derivatives, or enamel matrix protein derivatives (EMD) are derivatives of enamel matrix which include one or several enamel matrix proteins or parts of such proteins, produced naturally by alternate splicing or processing, or by either enzymatic or chemical cleavage of a natural length protein, or by synthesis of polypeptides in vitro or in vivo (recombinant DNA methods or cultivation of diploid cells, either plant or animal cells). Enamel matrix protein derivatives also include enamel matrix related polypeptides or proteins. The polypeptides or proteins may be bound to a suitable biodegradable carrier molecule, such as polyamine acids or polysaccharides, or combinations thereof. Furthermore, the term enamel matrix derivatives also encompasses synthetic analogous substances.

Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Dalton or more. Small proteins are called peptides or oligopeptides.

Enamel matrix proteins are proteins that normally are present in enamel matrix, i.e. the precursor for enamel (Ten Cate: Oral Histology, 1994; Robinson: Eur. 3. Oral Science, Jan. 1998, 106 Suppl. 1:282-91), or proteins which can be obtained by cleavage of such proteins. In general, such proteins have a molecular weight below 120,000 Dalton and include amelogenins, non-amelogenins, proline-rich non-amelogenins and tuftelins.

Examples of proteins for use according to the invention are amelogenins, proline-rich non-amelogenins, tuftelins, tuft proteins, serum proteins, salivary proteins, ameloblastin, sheathlin, and derivatives thereof, and mixtures thereof. A preparation containing an active enamel substance for use according to the invention may also contain at least two of the aforementioned proteinaceous substances. Moreover, other proteins for use according to the invention are found in the marketed product EMDOGAIN® (BIORA AB, Sweden).

EMDOGAIN® (BIORA AB, S-205 12 Malmö, Sweden) contains 30 mg enamel matrix protein, heated for 3 hours at about 80° C. in order to inactivate residual proteases, and 1 ml Vehicle Solution (Propylene Glycol Alginate), which are mixed prior to application, unless the protein and the Vehicle are tested separately. The weight ratio is about 80/8/12 between the main protein peaks at 20, 14 and 5 kDa, respectively.

In general, the major proteins of an enamel matrix are known as amelogenins. They constitute about 90% w/w of the matrix proteins. The remaining 10% w/w includes proline-rich non-amelogenins, tuftelins, tuft proteins, serum proteins and at least one salivary protein; however, other proteins may also be present such as, e.g., amelin (ameloblastin, sheathlin) which have been identified in association with enamel matrix. Furthermore, the various proteins may be synthesised and/or processed in several different sizes (i.e. different molecular weights). Thus, the dominating proteins in enamel matrix, amelogenins, have been found to exist in several different sizes that together form supramolecular aggregates. They are markedly hydrophobic substances that under physiologically conditions form aggregates. They may carry or be carriers for other proteins or peptides.

The amelogenins of developing dental enamel are tissue-specific proteins, rich in proline, leucine, histidine and glutamyl residues, and synthesised by the ameloblast cells of the inner enamel epithelium. These proteins comprise the bulk of the extracellular matrix that becomes mineralised with a hydroxyapatite phase to become the mature enamel. Examination of the amino acid sequences of amelogenins from a range of mammals shows a high degree of evolutionary sequence conservation, suggestive of specialised function. Recently it has been shown that multiple amelogenin components, observed in the matrix, arise both by a sequence of post-secretory proteolytic processing and by the expression of alternatively spliced mRNAs generated from the amelogenin gene(s) that are located on the sex chromosomes. Physico-chemical studies of recombinant amelogenins have shown that they undergo a self-assembly process in vitro generating supra-molecular 'nanosphere' structures, and recent observations in vivo point to a functional role for the nanospheres in the ultrastructural organization of the secretory enamel matrix, conducive to the organised development of the earliest mineral crystallites.

Recent studies of amelogenin expression have demonstrated that alternative-splicing of mouse amelogenin RNA generates seven distinct mRNAs, coding for amelogenin proteins from 194 to 44 amino acid residues in length.

Other protein substances are also contemplated to be suitable for use according to the present invention. Examples include proteins such as proline-rich proteins and polyproline. Other examples of substances that are contemplated to be suitable for use according to the present invention are aggregates of such proteins, of enamel matrix derivatives and/or of enamel matrix proteins as well as metabolites of enamel matrix, enamel matrix derivatives and enamel matrix proteins. The metabolites may be of any size ranging from the size of proteins to that of short peptides.

As mentioned above, the proteins, polypeptides or peptides for use according to the invention typically have a molecular weight of at the most about 120 kDa such as, e.g., at the most 100 kDa, 90 kDa, 80 kDa, 70 kDa or 60 kDa as determined by SDS PAGE electrophoresis.

The proteins for use according to the invention are normally presented in the form of a preparation, wherein the protein content of the active enamel substance in the preparation is in a range of from about 0.005% w/w to 100% w/w such as, e.g., about 0.5-99% w/w, about 1-95% w/w, about 10-95% w/w, about 10-90% w/w, about 15-90% w/w, about 20-90% w/w, about 30-90% w/w, about 40-85% w/w, about 50-80% w/w, about 60-70% w/w, about 70-90% w/w, or about 80-90% w/w.

A preparation of an active enamel substance for use according to the invention may also contain a mixture of active enamel substances with different molecular weights.

The proteins of an enamel matrix can be divided into a high molecular weight part and a low molecular weight part, and it has been found that a well-defined fraction of enamel matrix proteins possesses valuable properties with respect to treatment of periodontal defects (i.e. periodontal wounds). This fraction contains acetic acid extractable proteins generally referred to as amelogenins and constitutes the low molecular weight part of an enamel matrix (cf. EP-B-0 337 967 and EP-B-0 263 086).

In the present context, the active proteins are not restricted to the low molecular weight part of an enamel matrix. At present, preferred proteins include enamel matrix proteins such as amelogenin, tuftelin, etc. with molecular weights (as measured in vitro with SDS-PAGE) below about 60,000 Dalton but proteins having a molecular weight above 60,000 Dalton have also promising properties as candidates for promoting connective tissue growth.

Accordingly, it is contemplated that the active enamel substance for use according to the invention has a molecular weight of up to about 40,000 Da such as, e.g. a molecular weight of between about 5,000 Da and about 25,000 Da.

By separating the proteins, e.g. by precipitation, ion-exchange chromatography, preparative electrophoresis, gel permeation chromatography, reversed phase chromatography or affinity chromatography, the different molecular weight amelogenins can be purified.

The combination of molecular weight amelogenins may be varied, from a dominating 20 kDa compound to an aggregate of amelogenins with many different molecular weights between 40 and 5 kDa, and to a dominating 5 kDa compound. Other enamel matrix proteins such as tuftelin or proteolytic enzymes normally found in enamel matrix can be added and carried by the amelogenin aggregate.

Figure 2:
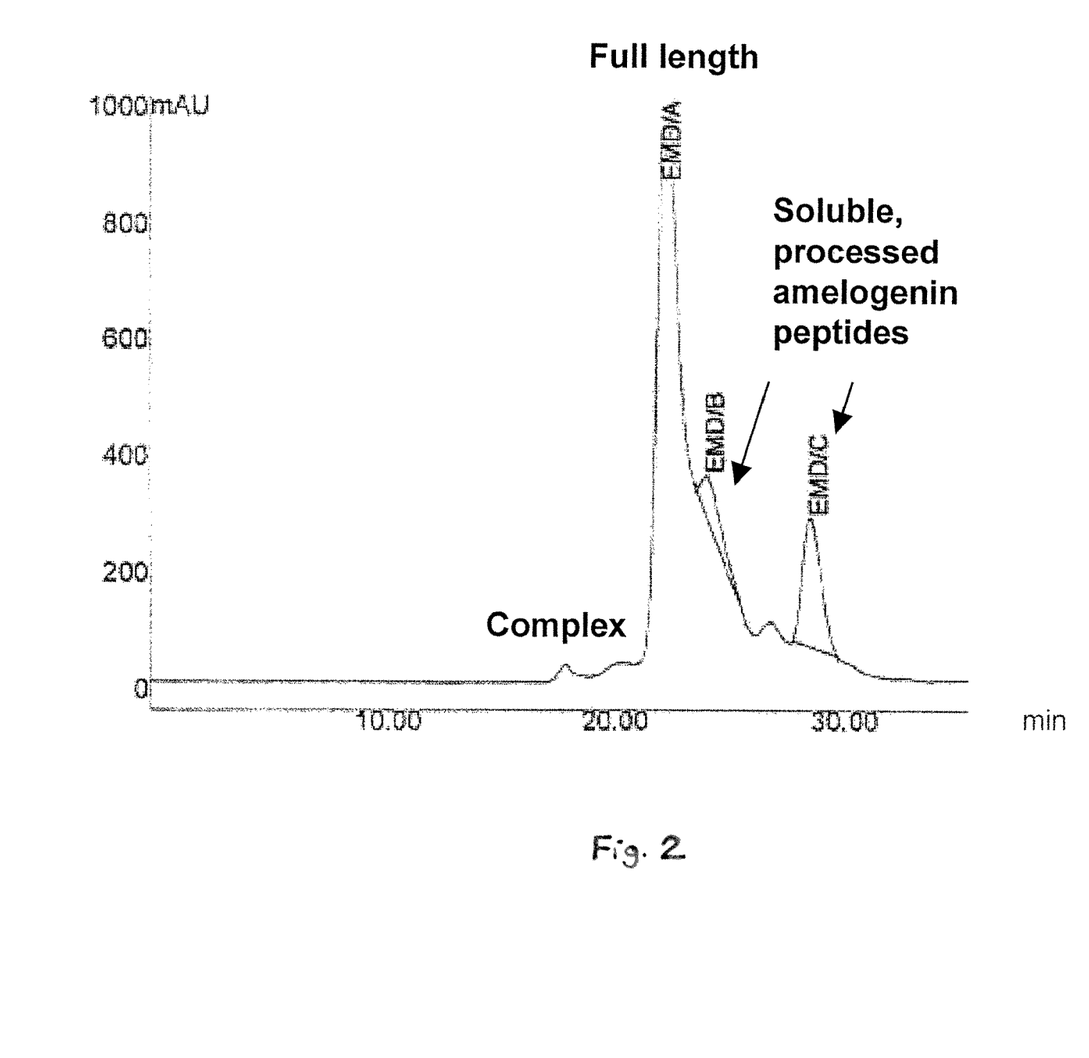

In an especially preferred embodiment of the present invention, said active enamel substance used for manufacturing a pharmaceutical composition for the prevention and/or treatment of a condition in a mammal, being characterised by an imbalance in the immune response of said mammal to an immunogen, is selected from the group consisting of any soluble amelogenin based peptide with an amino acid length between approximately 2-13 kDa, including a soluble amelogenin based peptide with an amino acid length between 2-4.5 kDa, 3-5.5 kDa, 4-6.5 kDa, 5-7.5 kDa, or 5-13 kDa, that is comprised in the eluate represented by the third and/or fourth peak of an HPLC analysis of processed amelogenin as shown in FIG. 2.

In a preferred embodiment of the present invention, said processed amelogenin product is a 5 k Da polypeptide.

In accordance to the present invention, an active enamel substance may be used together with other active drug substances such as, e.g. anti-bacterial, anti-inflammatory, antiviral, antifungal substances or in combination with local chemotherapy, inducers of apoptosis, growth factors such as, e.g., TGFβ, PDGF, IGF, FGF, EGF, keratinocyte growth factor or peptide analogues thereof. Enzymes—either inherently present in the enamel matrix or preparation thereof or added—may also be used in combination with an enamel matrix, enamel matrix derivative and/or enamel matrix protein, especially proteases.

For the administration to an individual (an animal or a human), an active enamel substance and/or a preparation thereof is preferably formulated into a pharmaceutical composition containing the active enamel substance and, optionally, one or more pharmaceutically acceptable excipients.

A composition comprising the active enamel substance to be administered may be adapted for administration by any suitable route, e.g. by systemic administration to a patient through a hose, syringe, spray or draining device. Furthermore, a composition may be adapted to administration in connection with surgery, e.g. as a systemic administration by infusion into the blood, lymph, ascites, or spinal fluids, or by inhalation.

In the following, examples of suitable compositions containing active enamel substances are given.

For the administration to an individual (an animal or a human) the substance(s) are preferably formulated into a pharmaceutical composition containing the substance(s) and, optionally, one or more pharmaceutically acceptable excipients.

The compositions may be in form of, e.g., fluid, semi-solid or solid compositions such as, e.g., but not limited to dissolved transfusion liquids, such as sterile saline, Ringer's solution, glucose solutions, phosphate buffer saline, blood, plasma or water, powders, microcapsules, microspheres, nanoparticles, sprays, aerosols, inhalation devices, solutions, dispersions, suspensions, emulsions, mixtures.

The compositions may be formulated according to conventional pharmaceutical practice, see, e.g., "Remington: The science and practice of pharmacy" $20^{th}$ ed. Mack Publishing, Easton Pa., 2000 ISBN 0-912734-04-3 and "Encyclopaedia of Pharmaceutical Technology", edited by Swarbrick, J. & J. C. Boylan, Marcel Dekker, Inc., New York, 1988 ISBN 0-8247-2800-9.

A pharmaceutical composition comprising an active substance serves as a drug delivery system. In the present context the term "drug delivery system" denotes a pharmaceutical composition (a pharmaceutical formulation or a dosage form) which upon administration presents the active substance to the body of a human or an animal. Thus, the term "drug delivery system" embraces plain pharmaceutical compositions such as, liquids, powders and sprays.

The choice of pharmaceutically acceptable excipients in a composition for use according to the invention and the optimum concentration thereof cannot generally be predicted and must be determined on the basis of an experimental determination thereof. Also whether a pharmaceutically acceptable excipient is suitable for use in a pharmaceutical composition is generally dependent on which kind of dosage form is chosen. However, a person skilled in the art of pharmaceutical formulation can find guidance in e.g., "Remington: The science and practice of pharmacy" $20^{th}$ ed. Mack Publishing, Easton Pa., 2000 ISBN 0-912734-04-3.

A pharmaceutically acceptable excipient is a substance, which is substantially harmless to the individual to which the composition will be administered. Such an excipient normally fulfils the requirements given by the national drug agencies. Official pharmacopoeias such as the British Pharmacopoeia, the United States of America Pharmacopoeia and the European Pharmacopoeia set standards for well-known pharmaceutically acceptable excipients.

In the following is given a review on relevant pharmaceutical compositions for use according to the invention. The review is based on the particular route of administration.

However, it is appreciated that in those cases where a pharmaceutically acceptable excipient may be employed in different dosage forms or compositions, the application of a particular pharmaceutically acceptable excipient is not limited to a particular dosage form or of a particular function of the excipient.

Parenteral Compositions:

For systemic application, the compositions according to the invention may contain conventionally non-toxic pharmaceutically acceptable carriers and excipients according to the including microspheres and liposomes.

The compositions for use according to the invention include all kinds of solid, semisolid and fluid compositions. Compositions of particular relevance are e.g. solutions, suspensions, emulsions.

The pharmaceutically acceptable excipients may include solvents, buffering agents, preservatives, chelating agents, antioxidants, stabilizers, emulsifying agents, suspending agents, diluents. For examples of the different agents see below.

In a most preferred embodiment, lyophilised powder of Emdogain® (BIORA AB, Malmö, Sweden) is dissolved in phosphate buffered saline (PBS) to a final concentration of 30 mg/ml.

Examples of other, equally preferred embodiments are lyophilised powder of Emdogain® (BIORA AB, Malmö, Sweden) dissolved in phosphate buffered saline (PBS) to a final concentration of 0.01-50 mg/ml, such as 0.01-10 mg/ml, 0.1-10 mg/ml, 0.01-5 mg/ml, 0.1-5 mg/ml, 0.01-1 mg/ml, 0.1-1 mg/ml, or 0.01-0.05 mg/ml, comprising concentrations of about 0.01 mg/ml, 0.02 mg/ml, 0.03 mg/ml, 0.04 mg/ml 0.05 mg/ml, 0.06 mg/ml, 0.07 mg/ml, 0.08 mg/ml, 0.09 mg/ml, 0.1 mg/ml, 0.2 mg/ml, 0.3 mg/ml, 0.4 mg/ml, 0.5 mg/ml, 1 mg/ml, 10 mg/ml, 20 mg/ml, 30 mg/ml, 35 mg/ml, 40 mg/ml, 45 mg/ml, or 50 mg/ml.

Furthermore, as documented in example 2, the weight of the dose of enamel matrix derivatives administered to the mammal in need thereof is of course adjusted to the individual bodyweight of the mammal to be treated, and the desired effectiveness of EMD, and will most preferably be in the range of about 0.01-100 mg EMD/kg bodyweight, such as about 0.01-50 mg EMD/kg, 0.05-10 mg EMD/kg 0.01-1 mg EMD/kg, 0.1-50 mg EMD/kg, 0.1-25 mg EMD/kg, 0.1-15 mg EMD/kg, or 0.1-10 mg EMD/kg, or 0.1-1 mg EMD/kg bodyweight, depending further on whether enamel matrix derivatives is to be applied at a high or a low dosage.

A typical low dosage will thus include at most 0.01, 0.02, 0.03, 0.04, 0.05, 0.06, 0.07, 0.08, 0.09, 0.1, 0.12, 0.15, 0.17, 0.2, 0.5, 1, 1.2, 1.5, 1.6, 1.8, 2, 2.5, 5, 6, 7, 8, 9, or 9.9 mg EMD/kg bodyweight, whereas a typical high dosage will include at least 10, 15, 18, 20, 25, 50, 75, or 100 mg EMD/kg bodyweight.

Dosages described above will be applied at least once/week, such as at least 1, 2, 3, 4, 5, 6, 7, or more times/week for at least 1-30 days, or alternatively for at least 10-90 days, or longer.

Examples of Various Agents:

Examples of solvents are but not limited to water, alcohols, blood, plasma, spinal fluid, ascites fluid and lymph fluid.

Examples of buffering agents are but not limited to citric acid, acetic acid, tartaric acid, lactic acid, hydrogenphosphoric acid, bicarbonates, phosphates, diethylamine etc.

Examples of chelating agents are but not limited to sodium EDTA and citric acid.

Examples of antioxidants are but not limited to butylated hydroxy anisole (BHA), ascorbic acid and derivatives thereof, tocopherol and derivatives thereof, cysteine, and mixtures thereof.

Examples of powder components are but not limited to alginate, collagen, lactose, powder which is able to form a gel when applied to a wound (absorbs liquid/wound exudate).

Examples of diluents and disintegrating agents are but not limited to lactose, saccharose, emdex, calcium phosphates, calcium carbonate, calcium sulphate, mannitol, starches and microcrystalline cellulose.

Examples of binding agents are but not limited to saccharose, sorbitol, gum acacia, sodium alginate, gelatine, starches, cellulose, sodium coboxymethylcellulose, methylcellulose, hydroxypropylcellulose, polyvinylpyrrolidone and polyetyleneglycol.

LEGENDS TO FIGURES

FIG. 1:

Whole blood samples treated with LPS, PepG and matrix protein compositions were incubated with 10 µl FITC or PE conjugated monoclonal antibodies. Expression of antigens were analysed by flow cytometry using 10 µl anti-CD14, anti-CD44, anti-ICAM-1, as well as isotype negative control anti-IgG$_1$ and anti-IgG$_2$. All samples are analysed on the FACScan using the CellQuest software.

FIG. 2:

Amelogenins were extracted from immature pig enamel according to Gestrelius et al. 1997. After solution in 30% acetonitril, the samples were separated on a Jasco HPLC using a size-exclusion column. The four distinct peaks represent the complex, the full length protein and the soluble, processed amelogenin peptides.

FIG. 3:

Enamel matrix derivatives caused decreased production of the pro-inflammatory cytokine tumour necrosis factor alpha (TNF-α), which was paralleled by increased release of the anti-inflammatory cytokine IL-10.

LISTING OF REFERENCES

1. Foster, S. J. 1992. Analysis of the autolysins of *Bacillus subtilis* 168 during vegetative growth and differentiation by using renaturing polyacrylamide gel electrophoresis. J Bacteriol. 174:464-70.
2. Gestrelius, S., C. Andersson, D. Lidstrom, L. Hammarstrom, and M. Somerman. 1997. In vitro studies on periodontal ligament cells and enamel matrix derivative. J Clin Periodontol. 24:685-92.
3. Hoang, A. M., T. W. Oates, and D. L. Cochran. 2000. In vitro wound healing responses to enamel matrix derivative [In Process Citation]. J Periodontol. 71:1270-7.
4. Petinaki, E., S. Nikolopoulos, and E. Castanas. 1998. Low stimulation of peripheral lymphocytes, following in vitro application of Emdogain. J Clin Periodontol. 25:715-20.

EXPERIMENTAL SECTION

Experiment 1

The aim of the present study was to investigate potential modulatory effects of amelogenin on innate immune mechanisms in human whole blood. Of particular interest was the cytokine release and regulation of inflammatory surface receptors in response to bacterial cell wall products.

Materials and Reagents.

Peripheral venous blood was obtained from healthy staff members and collected in vacutainers containing 0.129 M CitNa (Becton Dickinson Vacutainer Systems Eur, Meylan Cedex, France). Lyophilised powder of Emdogain® (BIORA AB, Malmö, Sweden) was dissolved in phosphate buffered saline (PBS) to a final concentration of 30 µg/ml. *Escherichia coli* 026:B6 lipopolysaccharide (LPS; Difco Laboratories, Detroit, Mich., USA) was suspended in pyrogen free sterile saline and 10 ng/ml of LPS added directly to the blood samples in microcentrifuge tubes. Lipoteichoic acid (LTA) was purchased from Sigma chemicals (St. Louis, Miss., USA). Peptidoglycan (PepG) was isolated from *Staphylococcus aureus*, as previously described (Foster, S. J. 1992 J Bacteriol. 174:464-70). Analysis of the autolysines of *Bacillus subtilis* 168 during vegetative growth and differentiation was performed by using renaturing polyacrylamide gel electrophoresis, the autolysines were added directly to the blood samples at a concentration of 10 µg/ml.

Whole Blood Experiments.

Peripheral venous blood was obtained from healthy staff members and collected in vacutainers containing 0.129 M CitNa (Becton Dickinson Vacutainer Systems Eur, Meylan Cedex, France). The whole blood samples were aliquoted into 1.5 ml microcentrifuge tubes (Sorenson, BioScience Inc., Salt Lake City, Utah, USA). Prior to stimulation with LPS, PepG or LTA, the blood samples were preincubated at 37 C for 2 h with dissolved Emdogain® at a final concentration of 0, 45, 150, 300, 450, 600, or 750 g/ml.

The blood samples were then stimulated with 10 ng/ml of LPS, 10 g/ml PepG or 100 g/ml LTA for 4 or 6 h, alternatively. The blood was subsequently cooled on ice and centrifuged (14,000 g for 1 min), and plasma pipetted off for cytokine protein detection. As controls, equivalent volumes of 0.9% NaCl were added instead of the bacterial products. Basal cytokine levels were investigated immediately after blood drainage.

Preliminary studies had shown that PepG and LTA give peak values of TNF-a, 6 h after stimulation, compared to 4 h with LPS stimulation. Accordingly, 4 h of LPS stimulation and 6 h of PepG and LTA stimulation were chosen.

ELISA technique. Plasma concentrations of TNF-$\alpha$, IL-6 and IL-10 is determined with a commercially available solid-phase sandwich enzyme linked immunosorbent assay (ELISA) kit (PeliKine Compact, CLB Labs, Amsterdam, The Netherlands) according to the manufacturer's instructions. The detection limit of the TNF-$\alpha$, IL-6 and IL-10 ELISA is 3, 0.4 and 3 pg/ml, respectively. The plates are read at 450 nm in an ELISA reader (Thermo max microplate reader, Molecular Devices, Menlo Park, Calif., USA).

Figure 1:
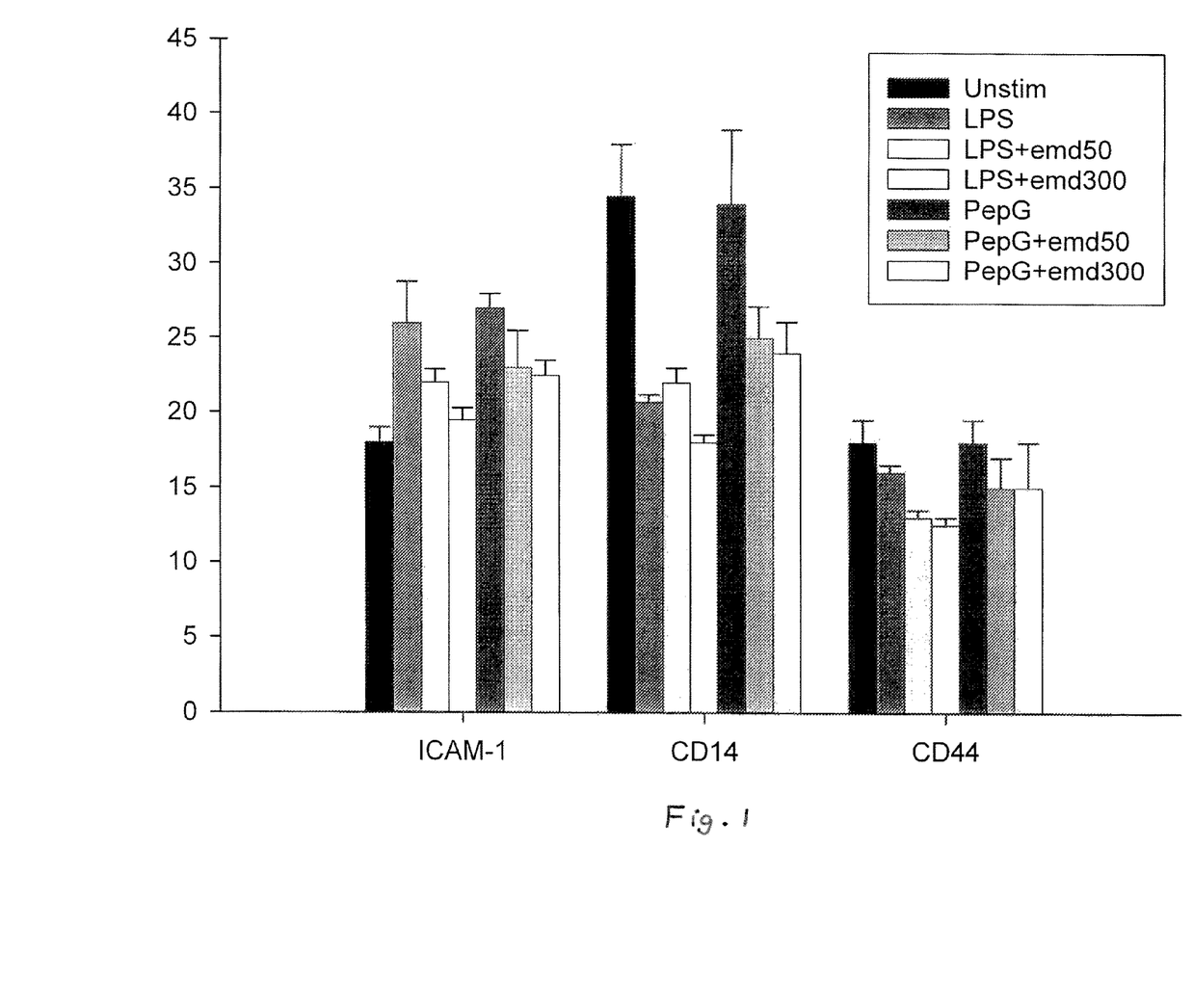

Antibody labelling and flow cytometry. Subsequent to stimulation, whole blood samples are immediately aliquoted in 100 µl into Falcon polystyrene tubes (Becton Dickinson, Lincoln Park, N.J., USA) and incubated with 10 µl FITC or PE conjugated monoclonal antibodies in darkness for 30 minutes at room temperature. Prior to washing and fixation, red blood cells are lysed using FACS Lysing Solution (Becton Dickinson, San Jose, Calif., USA). The samples are washed three times with CellWash (Becton Dickinson) before fixation with formaldehyde 1% (CellFIX, Becton Dickinson, Erembodegem, Belgium). Expression of antigens are analysed by flow cytometry using 10 µl anti-CD14 (18D11, Diatec AS, Oslo, Norway), anti-CD44 (Diatec AS, Oslo, Norway), anti-ICAM-1 (Diatec AS, Oslo, Norway), as well as isotype negative control anti-IgG$_1$ (1B9) and anti-IgG$_2$ (5A7) (both Diatec AS). All samples are analysed on the FACScan (Becton Dickinson) using the CellQuest software. The results are represented in FIG. 1.

In each experiment, the monocyte population is identified as CD14 positive cells with characteristic location in the scatter diagram. Fluorescence intensity (FI) is measured in the monocyte population after appropriate gating according to these features, and mean FI (geometric mean) is recorded for each measurement.

Statistical Analyses. Data is presented as means±standard error of the mean (SEM). The data are analysed by 1-way analysis of variance (ANOVA) followed by the Tukey test. P<0.05 is considered significant.

Figure 3:
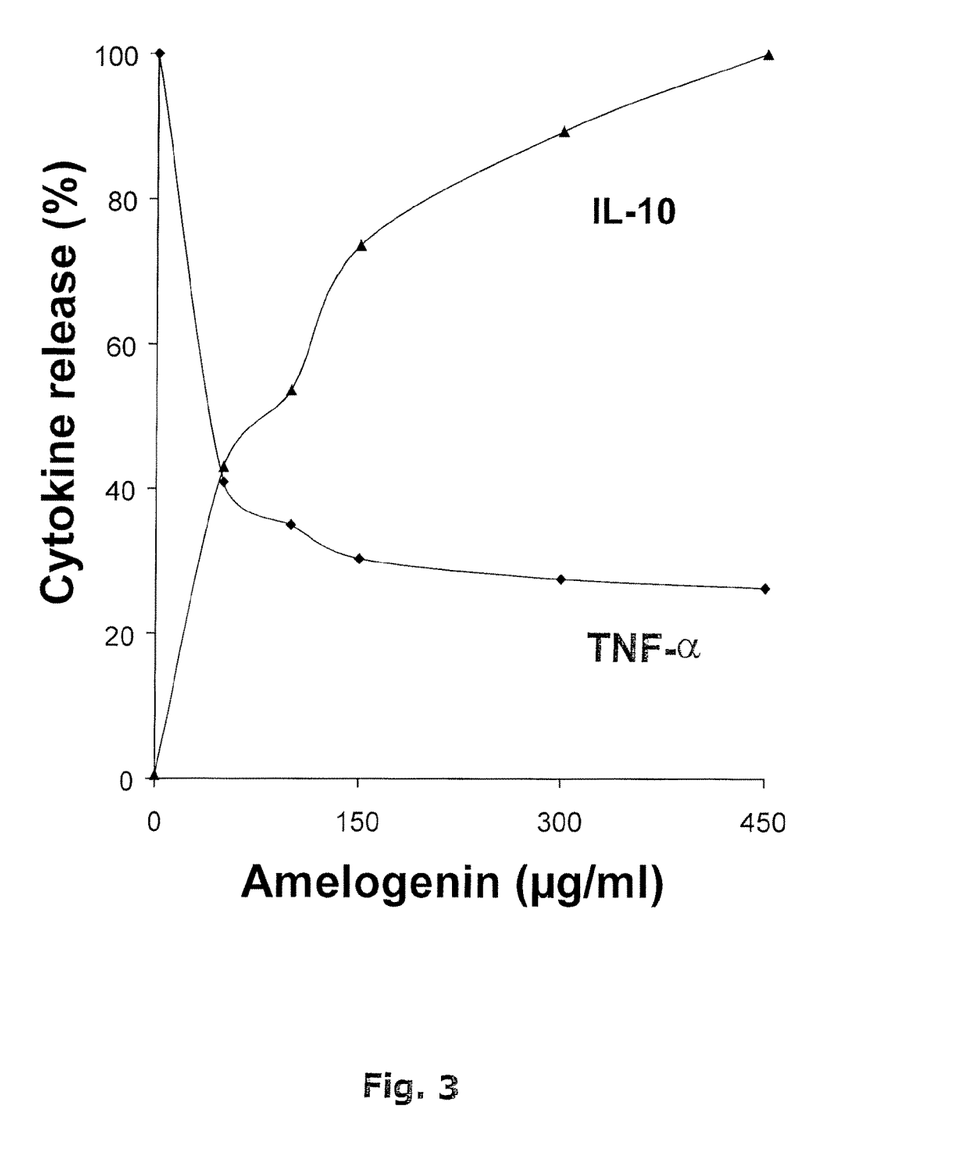

As seen in FIG. 3, enamel matrix derivatives caused decreased production of the pro-inflammatory cytokine tumour necrosis factor alpha (TNF-$\alpha$), which was paralleled by increased release of the anti-inflammatory cytokine IL-10. The results indicate that enamel matrix derivatives have potent immunomodulatory properties. It is also tempting to suggest that enamel matrix derivatives may have therapeutic potentials in sepsis with multiple organ failure. In addition, enamel matrix derivatives may have a therapeutic potential in other diseases associated with acute or chronic inflammation, such as inflammatory bowel disease, rejection of transplanted organs or orthopaedic implants, rheumatoid arthritis, arteriosclerosis and several others.

Experiment 2

In this study using a pig model of sepsis, the therapeutic potential of enamel matrix derivatives was examined in vivo. The model is based on continuous infusion of *E. Coli* LPS, giving rise to an acute inflammatory response. After a while (typically after half to one hour of LPS injection) the animal enters into septic shock mirroring important pathophysiological features of severe sepsis. The model is a powerful tool linking in vitro findings with possibly clinical trials.

Enamel matrix derivatives (max dosage 5 mg/kilo bodyweight, i.e. a calculated serum concentration of about 100 mg/l) were administered by an i.v. bolus injection to the pigs 30 minutes before onset of sepsis (=injection of LPS, 1.7 µg/kilo bodyweight/hour). The half life for enamel matrix derivatives in blood is reported to be 240 minutes. Thus, to maintain a therapeutic serum level of EMD, an i.v. transfusion set up was used to deliver 50 mg enamel matrix derivatives in 100 ml Ringer's solution (pH=6) per hour. For control, three "sham" pigs are treated identically, except for administration of EMD, which was substituted with injection and transfusion with serum albumin ("placebo").

Haemodynamic parameters were registered continuously, with hourly recordings until end of experiment at 5 h after infusion of bacterial toxins (LPS). Blood samples and recording of clinical parameters were taken before the experiment's start (time zero), immediately after start of enamel matrix derivatives or placebo injection (time zero-a), immediately after start of LPS injection (time one) and every hour after onset of sepsis from the hepatic and portal vein, the abdominal artery, and the pulmonary artery, and analysed for blood homeostasis parameters, organ function markers (serum aspertate aminotransferase (ASAT), serum alanine aminotransferase (ALAT), and serum alkaline phosphatase activity as markers for liver function, and gamma-glutamyltransferase ($\gamma$-GT) and Creatinine as marker for kidney function) and inflammatory mediators (TNF-$\alpha$, IL-1$\beta$ and IL-6). The organ function markers were analysed in blood sampled from the pig hourly during the experiment at predefined time points. The blood samples were analysed using standard hospital procedures in the haematological laboratory of the Norwegian National Hospital. The inflammatory markers were analysed in the same blood samples by the use of ELISA, applying the Porcine TNF-α/TNFSF2 Quantikine P ELISA kit (#PTA00), the Porcine IL-6 Quantikine P immunoassay kit (#P6000), and the Porcine IL-1β/IL-1F2 Quantikine P ELISA kit (#PTA00), all from R&D Systems Inc. (Minneapolis, Minn., USA). The standard procedures from the manufacturer were used without omissions or adaptations.

After the experiment was completed (death of the animal, or after 5 hours with continuous injections of enamel matrix derivatives or placebo and LPS), the animals were euthanised and necropsy performed. Internal circulatory organs were examined macroscopically and tissues were sampled for histological evaluation according to the research plan.

Results

Pig 1

Physical data: Female; 23.5 kg total bodyweight; Healthy
Surgery: No complications Treatment: Placebo (25 mg serum albumin in 50 ml PBS bolus injection, 10 mg SA. in 100 ml Ringer's solution per hour transfusion, total SA dosage=75 mg), LPS (40 μg/hour in 4.5 ml PBS, continuous injection for 5 hours; total LPS dosage=200 μg).

Haemodynamic observations: The animal showed no response to placebo injection. A strong initial response to LPS injection was observed followed by a septic shock condition that lasted throughout the experiment. The onset of shock was before one hour after initiation of LPS injection.

Anatomy and macroscopic appearance of circulatory organs at death: All circulatory organs had normal anatomy. Signs of pathology was observed in the liver which showed signs of congestion and haemostasis.

Haematology: The animal initially showed normal haematological values. Most values stayed within the normal range throughout the experiment. The only exception was observed at four and five hours after LPS injection, when an increase in B-neutrophiles and a decrease in B lymphocytes was observed.

Biochemistry: All enzyme activities and Creatinine stayed within normal values throughout the experiment. A slow but steady decrease in creatinine was observed, but the values never decreased below the norm. The pig initially showed a slight increase in ALP, but this normalized before LPS was administered. ASAT values were also on the high side throughout the experiment, but did not show any significant change from LPS injection.

Cytokines: The pig showed a rapid increase in TNF values after administration of LPS. The value peaked above detection limit (1500 μg/l) before one hour after start of LPS injection and stayed at this level throughout the experiment. Also IL-6 increased rapidly following the onset of LPS injection. The IL-6 level increased steadily all the way through the experiment ending at a level of 3500 μg/l. IL-1β showed a slow increase caused by the LPS injection, ending at about 700 μg/l after 5 hours.

Comments: Haemodynamic parameters indicated hepatic and lung failure towards the end of the experiment. Low and declining diuresis indicated renal insufficiency. First signs of organ insufficiency was observed at two hours after LPs injection started. Tremor was observed from 30 minutes after LPS administration. Haematology and biochemistry values indicated that the life support systems were operated correctly, and that the observed effects were caused by the toxin injection and not by trauma from surgery. The Inflammatory status indicated that the pig was suffering from a septic shock. There were no signs of recovery in the cytokine values. It is very unlikely that this pig could have survived the experiment.

Pig 2

Physical data: Female; 21.5 kg total bodyweight; Healthy
Surgery: No complications Treatment: Enamel matrix derivatives (21.5 mg enamel matrix derivatives in 50 ml PBS bolus injection, 10 mg enamel matrix derivatives in 100 ml Ringer's solution per hour transfusion, total enamel matrix derivatives dosage=71.5 mg), LPS (37 μg/hour in 4.5 ml PBS, continuous injection for 5 hours; total LPS dosage=185 μg).

Haemodynamic observations: The animal showed no response to the bolus injection of EMD. A very rapid and strong initial response to LPS injection was observed (tachycardia and increased arterial flow) followed by an onset of a septic shock condition at about one hour after start of LPS injection. At this stage, early signs or multi-organ failure was observed. However, at later time points the haemodynamic values stabilized and organ functions recovered.

Anatomy and macroscopic appearance of circulatory organs at death: All circulatory organs had normal anatomy. Macroscopic signs of pathology were not observed in organs examined.

Haematology: The animal initially showed normal haematological values. All values stayed within the normal range throughout the experiment.

Biochemistry: All enzyme activities and creatinine stayed within normal values throughout the experiment. The pig initially showed a slight increase in ALP, but this stayed unchanged by enamel matrix derivatives or LPS injections. ASAT values increased slightly towards the very end of the experiment, but did not show any significant change from enamel matrix derivatives or LPS injection.

Cytokines: Enamel matrix derivatives injection did not provoke any increase in the analysed circulating cytokines. However, the pig showed a rapid increase in TNF values after administration of LPS. The value peaked above detection limit (1500 μg/l) before one hour after start of LPS injection and stayed at this level for about four hours. After four hours, the TNF value decreased and showed sign of normalizing. Also IL-6 increased rapidly following the onset of LPS injection. The IL-6 level increased steadily through the experiment peaking at 4800 μg/l after four hours. After five hours the IL-6 values seemed to decrease, but because of the (planned) termination of the experiment, this trend was not confirmed. IL-1β showed a slow increase caused by the LPS injection, ending at about 1000 μg/l after 5 hours.

Comments: The animal seemed to recover from an obvious septic shock and onset of organ failure, as observed both by haemodynamic parameters and by recovery of renal function (diuresis) and reduction in ascites. Tremor occurred from one hour after LPS administration. These findings are uncommon, especially following such a strong initial response to endotoxin (LPS). Haematology and biochemistry values indicated that the life support systems were operated correctly, and that the observed effects were caused by the toxin injection and not by trauma from surgery. The Inflammatory status indicated that the pig initially was suffering from a septic shock. There were, however, signs of slow recovery in the IL-6 and TNF values. IL-1β values seemed unaffected by enamel matrix derivatives administration. Given time and a continuing decrease in the inflammatory cytokine levels, this pig would most likely have survived the experiment.

Pig 3

Physical data: Female; 25.0 kg total bodyweight; Healthy
Surgery: No complications Treatment: Placebo (125 mg SA. in 100 ml PBS bolus injection, 50 mg SA. in 100 ml Ringer's solution per hour transfusion, total SA dosage=375 mg), LPS (43 µg/hour in 4.5 ml PBS, continuous injection for 5 hours; total LPS dosage=215 µg).

Haemodynamic observations: The animal showed no response to the placebo injection. A low to medium initial response to LPS injection was observed followed by a septic shock condition that lasted throughout the experiment. The onset of shock was about one hour after initiation of LPS injection.

Anatomy and macroscopic appearance of circulatory organs at death: All circulatory organs had normal anatomy. Signs of pathology were only observed in the liver which showed signs of congestion (swelling and redness) and haemostasis.

Haematology: The animal initially showed normal haematological values. Most values stayed within the normal range throughout the experiment. The only exception was observed at four and five hours after LPS injection, when an increase in B-neutrophiles and a decrease in B lymphocytes was observed.

Biochemistry: Most enzyme activities stayed within normal values throughout the experiment. A slow but steady decrease in creatinine was observed, and after two hours after LPS injection, the creatinine level decreased below the normal range and stayed low for the rest of the experiment. The pig initially showed an increased ALP activity, but this value was stable and unaffected by the LPS injection. The Inflammatory status indicated that the pig was suffering from a septic shock. There were no signs of recovery in the cytokine values. It is very unlikely that this pig could have survived the experiment.

Cytokines: The pig showed a rapid increase in TNF values after administration of LPS. The value peaked above detection limit (1500 µg/l) before one hour after start of LPS injection and stayed at this level throughout the experiment. Also IL-6 increased rapidly following the onset of LPS injection. The IL-6 level increased steadily all the way through the experiment peaking at 5000 µg/l at three hours after LPS injection, ending at a level of 3900 µg/l. IL-1β showed a slow increase caused by the LPS injection, ending at about 700 µg/l after 5 hours.

Comments: Haemodynamic parameters indicated hepatic failure towards the end of the experiment. Low diuresis indicate renal insufficiency. Signs of organ failure were observed from three hours on after LPS injection started. Tremor was evident 30 minutes after LPS administration. Haematology and biochemistry values indicated that the life support systems were operated correctly, and that the observed effects were caused by the toxin injection and not by trauma from surgery. The Inflammatory status indicated that the pig was suffering from a septic shock. There were no signs of recovery in the cytokine values. It is very unlikely that this pig could have survived the experiment.

Pig 4

Physical data: Female; 24.5 kg total bodyweight; Healthy
Surgery: No complications Treatment: Enamel matrix derivatives (125 mg enamel matrix derivatives in 100 ml PBS bolus injection, 50 mg enamel matrix derivatives in 100 ml Ringer's solution per hour transfusion, total enamel matrix derivatives dosage=375 mg), LPS (42 µg/hour in 4.5 ml PBS, continuous injection for 5 hours; total LPS dosage=210 µg).

Haemodynamic observations: The animal showed no response to the bolus injection of EMD. A strong initial response to LPS injection was observed followed by a weak septic shock condition at about three hours after start of LPS injection. At this stage early signs or lung failure were observed. However, at later time points, the haemodynamic values stabilized and all organ functions recovered.

Anatomy and macroscopic appearance of circulatory organs at death: All circulatory organs had normal anatomy. Macroscopic signs of pathology were not observed in organs examined.

Haematology: The animal initially showed normal haematological values. All values stayed within the normal range throughout the experiment.

Biochemistry: All enzyme activities and creatinine stayed within normal values throughout the experiment. The pig initially showed a slightly increased ALP activity, but this stayed unchanged by enamel matrix derivatives or LPS injections. ASAT values increased slightly towards the very end of the experiment, but did not show any significant change directly associated with the enamel matrix derivatives or LPS injection.

Cytokines: Enamel matrix derivatives injection did not provoke any increase in the analysed circulating cytokines. However, the pig showed a rapid increase in TNF values after administration of LPS. The value peaked above detection limit (1500 µg/l) before one hour after start of LPS injection and stayed at this level throughout the experiment. Also IL-6 increased rapidly following the onset of LPS injection. The IL-6 level increased steadily through the experiment rising above detection level (>5000 µg/l) after three hours. At four hours the IL-6 values seemed to decrease, and this trend was confirmed also at five hours. IL-1β showed a slow, steady increase caused by the LPS injection, ending at about 700 µg/l after 5 hours.

Comments: The animal seemed to be protected from severe septic shock and organ failure, as observed both by clinical and haemodynamic parameters. No organ failure was observed, but diuresis was low throughout the experiment. There was only minute production of ascites, and no tremor was observed. These findings are uncommon, especially following a strong initial response to endotoxin (LPS). Haematology and biochemistry values indicated that the life support systems were operated correctly, and that the observed effects were caused by the toxin injection and not by trauma from surgery. The Inflammatory status indicate that the pig initially suffered from onset of a septic shock. There were, however, signs of slow recovery in the IL-6 and TNF values. IL-1β values seemed unaffected by enamel matrix derivatives administration. Given time and a continuing decrease in the inflammatory cytokine levels, and the good haemodynamic condition, it is believed that this pig would have survived the experiment.

Pig 5

Physical data: Female; 25.0 kg total bodyweight; Healthy
Surgery: No complications Treatment: Enamel matrix derivatives (125 mg enamel matrix derivatives in 100 ml PBS bolus injection, 50 mg enamel matrix derivatives in 100 ml Ringer's solution per hour transfusion, total enamel matrix derivatives dosage=375 mg), LPS (43 µg/hour in 4.5 ml PBS, continuous injection for 5 hours; total LPS dosage=215 µg).

Haemodynamic observations: The animal showed an initial increase of lung blood pressure as response to the very start of bolus injection of EMD. The effect was very transient (minutes) and not dosage dependent, indicating that the enamel matrix derivatives solution had a brief vasoconstrictive effect on the lung capillaries. The observed effect was normalized before the bolus injection was completed. No other effects was observed from the enamel matrix derivatives injection. This animal did not show any profound response to LPS injection at all. No signs of a septic shock condition was observed and organ circulation was stable throughout the experiment. The LPS flow and the position of the LPS catheter was controlled several times during the experiment to ensure that LPS was delivered according to the experimental plan.

Anatomy and macroscopic appearance of circulatory organs at death: All circulatory organs had normal anatomy. Macroscopic signs of pathology was not observed in organs examined.

Haematology: The animal initially showed normal haematological values, except for the count of white blood cells that was significantly increased (twice the normal value) from the start of surgery (0-sample). The relative levels of the different white blood cells appeared normal however, and remained stable during the experiment. All other values stayed within the normal range throughout the experiment.

Biochemistry: All enzyme activities and creatinine stayed within normal values throughout the experiment, except for ALP, which level was increased from the start of the experiment, but remained stable throughout the observation period. The ALP level remained unchanged by enamel matrix derivatives or LPS injections. ASAT values increased slightly from LPS injection to the end of the experiment. This increase was however very small and peaked barely above the normality limit.

Cytokines: Enamel matrix derivatives injection did not provoke any increase in the analysed circulating cytokines. However, this pig showed a significantly increased TNF value even before the experiment started (>1500 µg/l). This value stayed above detection range until 2 hours after administration of LPS. However, from then on a rapid decrease in TNF values was observed, and the TNF level was nearly normalized before the end of the experiment. IL-6 increased rapidly following the onset of LPS injection. The IL-6 level increased steadily until two hours after LPS injection peaking at 2500 µg/l. The IL-6 levels then tapered off, reaching normal level at five hours after LPS injection. IL-1β showed a slow, steady increase caused by the LPS injection, ending at about 900 µg/l after 5 hours.

Comments: The animal seemed to be completely protected from LPS induced septic shock and organ failure, as observed both by clinical and haemodynamic parameters. No organ failure was observed, and diuresis was good and stable throughout the experiment. There was only minute production of ascites, and no tremor was observed. It is extremely uncommon that animals fail to respond to central endotoxin (LPS) injections in this way. Haematology and biochemistry values indicated that the life support systems were operated correctly, and that the observed effects were caused by the toxin injection and not by trauma from surgery. The Inflammatory status indicate that the pig initially suffered from a weak onset of septic shock. There was however, clear signs of rapid recovery in the IL-6 and TNF values. IL-1β values seemed unaffected by enamel matrix derivatives administration. There is little doubt that this animal, if allowed, would have survived the experiment.

Pig 6

Physical data: Female; 23.0 kg total bodyweight; Healthy

Surgery: No complications

Treatment: Enamel matrix derivatives (115 mg enamel matrix derivatives in 100 ml PBS bolus injection, 50 mg enamel matrix derivatives in 100 ml Ringer's solution per hour transfusion, total enamel matrix derivatives dosage=365 mg), LPS (39 µg/hour in 4.5 ml PBS, continuous injection for 5 hours; total LPS dosage=195 µg).

Haemodynamic observations: The animal showed an initial increase of lung blood pressure as response to the bolus injection of EMD. The response was spontaneous and transient (minutes) and not dosage dependent, indicating that enamel matrix derivatives injection had a brief vasoconstrictive effect on the lung capillaries. The effect was normalized before the bolus injection was completed.

A strong initial response to LPS injection was observed (rapid, transient increase in heart rate and arterial flow), followed by a moderately hyperbar condition that lasted throughout the experiment. No signs of septic shock was observed, nor were there any signs of organ failure.

Anatomy and macroscopic appearance of circulatory organs at death: All circulatory organs had normal anatomy. Macroscopic signs of pathology was not observed in organs examined.

Haematology: The animal initially showed normal haematological values. All values stayed within the normal range throughout the experiment.

Biochemistry: All enzyme activities and creatinine stayed within normal values throughout the experiment, except for ALP and ASAT that were slightly increased from the start of the experiment, but remained stable throughout the observation period. The ALP and ASAT levels remained unchanged by enamel matrix derivatives or LPS injections.

Cytokines: Enamel matrix derivatives injection did not provoke any increase in the analysed circulating cytokines. However, the pig showed a rapid increase in TNF values after administration of LPS. The value peaked above detection limit (1500 µg/l) before one hour after start of LPS injection and stayed at this level for about three hours. After three hours, the TNF value decreased rapidly, and normalized at the end of the observation period. Also IL-6 increased rapidly following the onset of LPS injection. The IL-6 level peaked at 2700 µg/l, two hours after LPS injection. However, at the end of the experiment the IL-6 value had decreased to nearly normal value (350 µg/l). IL-10 showed a slow, steady increase caused by the LPS injection, peaking at about 1200 µg/l after 4 hours.

Comments: This animal seemed to be protected from severe septic shock and organ failure, as observed both by haemodynamic and clinical parameters. No organ failure was observed and diuresis was high and stable throughout the experiment. There was only minute production of ascites, and tremor was observed only after about four hours of LPS infusion. These findings are uncommon, especially following a strong initial response to endotoxin (LPS), as observed here. Haematology and biochemistry values indicated that the life support systems were operated correctly, and that the observed effects were caused by the toxin injection and not by trauma from surgery. The inflammatory status indicated that the pig initially suffered from a of strong septic shock (rapid, strong increase in TNF and IL-6). There were, however, clear signs of total remission in the IL-6 and TNF values. IL-1β values seemed unaffected by enamel matrix derivatives administration. There is little doubt that this animal, if allowed, would have survived the experiment.

SUMMARY

Controls (Pig 1 and 3)

The controls both behaved normally, i.e. they both entered into a septic shock situation after about 30 minutes after the onset of LPS injection. Both pigs survived 5 hours of LPS injection, however, they showed clear clinical signs of severe, uncontrolled septic shock with increased temperature, multi-organ failure, renal insufficiency, hypotension and reduced cardiac output. Also analysis of the blood showed clear signs of septic shock. The inflammatory status also matched an acute toxin induced septic shock with strong expression of both TNF-α and Interleukin-6. The condition of these pigs towards the end of the experiment was so severe that it was judged to be incompatible with continued living.

Low Enamel Matrix Derivatives Dosage (Pig 2)

The pig administered the low enamel matrix derivatives dosage also entered into a septic shock situation. However, the onset of the acute inflammatory response to LPS was delayed with about 30-60 minutes when compared to the sham animals. After the onset of sepsis, the pig stabilized and then slowly recovered from the shock. This animal showed slightly better clinical parameters and did not show signs of renal failure (as measured by diuresis). The pig was euthanised as planned 5 hours after onset of LPS injection.

The bolus injection and the following transfusion with a "low" dosage of enamel matrix derivatives did not provoke any clinical signs of adverse reactions in this pig, nor did any monitored parameter respond to the enamel matrix derivatives injection.

This pig also showed a decreasing trend in TNF and IL-6 values. This observation, together with the clinical observations suggest that the animal was recovering from the shock.

High Enamel Matrix Derivatives Dosage (Pig 4, Pig 5 and Pig 6)

None of the three animals administered high enamel matrix derivatives dosages did experience a severe septic shock situation from the LPS injection. Two animals (pig 4 and pig 6) experienced an initial, but transient endotoxin response, but the situation quickly stabilized and the animals quickly recovered and remained "controlled" throughout the experiment. The third animal (pig 5) did not respond to the LPS injection at all. None of these animals showed signs of multi-organ failure or renal insufficiency. Only one of the pigs (pig 6) experienced the typical tremor induced by LPS injection. The onset of tremor was significantly delayed (4 hours), as compared to the controls. The pigs were euthanised as planned 5 hours after the initiation of LPS injection.

The bolus injections and the following transfusion with "high" dosages of enamel matrix derivatives did not provoke any persistent clinical signs or adverse reactions in these pigs. In two of the pigs (pig 5 and pig 6), an initial response to the bolus injection was observed. This response was observed as a rapid, but transient increase in pulmonary arterial pressure indicating that the central bolus injection of the high concentration enamel matrix derivatives solution (ca. 1.25 mg/ml) induced a spontaneous constriction of pulmonary arterioles and/or capillaries. The effect was immediate, and was not dosage related. The observed effect normalized within minutes and the pigs were stable, showing normal haemodynamic parameters and clinical status before the completion of the bolus injection.

These pigs also showed a decreasing trend in TNF and IL-6 values after the initial LPS response. In fact, in two of the three animals (pig 5 and pig 6) the TNF and IL-6 values nearly normalized before the end of the observation period. This observation, together with the clinical observations, suggest that these animals were protected from the LPS induced shock and subsequent multi organ failure. The enamel matrix derivatives injection administered in these pigs protected the animals from severe damage from the toxin injection, and thus rescued the animals from experiencing a septic shock. All three animals would have survived the experiment.

The invention claimed is:

1. A method of treating a mammal for systemic inflammatory response syndrome, said method comprising administering parenterally to said mammal a composition comprising from 0.01 mg/ml to 1 mg/ml amelogenin proteins.

2. The method according to claim 1, wherein the systemic inflammatory response syndrome results from shock, burns, extensive surgical procedures, traumatic injury, dialysis, and bacterial or viral infection.

3. The method according to claim 1, wherein the systemic inflammatory response syndrome results from a disease selected from the group consisting of extracorporeal membrane oxygenation, shock, sepsis, multi organ failure, rejection of an implant, rejection of an organ, rejection of a prosthesis, heart and lung bypass surgery, chronic inflammation, asthma, stress related disease in the lung, gangrene, soft tissue infection and wound infection.

4. The method according to claim 1, wherein the systemic inflammatory response syndrome is caused by a bacterium selected from the group consisting of gram negative microbes and gram positive microbes.

5. The method according to claim 4, wherein said systemic inflammatory response syndrome is caused by an endo-toxin or an exo-toxin produced by said microbe.

6. The method according to claim 5, wherein the systemic inflammatory response syndrome is caused by PepG from *Staphylococcus aureus*.

7. The method according to claim 5, wherein the systemic inflammatory response syndrome is caused by an LPS from *Escherichia coli*.

8. The method according to claim 1, wherein the amelogenin proteins are of porcine origin.

9. The method according to claim 1, wherein the amelogenin proteins are of synthetic origin.

10. The method according to claim 1, wherein the mammal is human.

11. The method according to claim 1, wherein the composition further comprises one or more of the following: proline-rich non-amelogenins, tuftelins, tuft proteins, serum proteins, salivary proteins, ameloblastins, sheathlins, and mixtures thereof.

12. The method according to claim 1, wherein the composition further comprises one or both of proline-rich proteins or poly-proline proteins.

13. The method according to claim 1, wherein the composition is administered by continuous injection.

14. The method according to claim 1, wherein the composition is administered as a bolus injection.

15. The method according to claim 1, wherein the composition comprises a pharmaceutically acceptable excipient.

16. The method according to claim 15, wherein the pharmaceutically acceptable excipient is phosphate buffer saline.

17. The method according to claim 1, further comprising administering one or more active drug substances with said composition.

18. The method according to claim 17, wherein the one or more active drug substances are independently selected from the group consisting of: anti-bacterial, anti-inflammatory, antiviral, antifungal, inducers of apoptosis, growth factors, keratinocyte growth factors, and peptide analogs thereof.

19. The method of claim 1, wherein the composition is administered in combination with local chemotherapy.

* * * * *